(12) United States Patent
Iiyama et al.

(10) Patent No.: US 6,619,959 B2
(45) Date of Patent: Sep. 16, 2003

(54) PROCESS FOR PREPARING DENTAL PROSTHESIS

(75) Inventors: Kenichi Iiyama, Tokyo (JP); Yuki Sakamoto, Tokyo (JP); Tatsuru Doumoto, Tokyo (JP)

(73) Assignee: GC Corporation, Tokyo (JP)

( * ) Notice: Subject to any disclaimer, the term of this patent is extended or adjusted under 35 U.S.C. 154(b) by 73 days.

(21) Appl. No.: 10/051,080

(22) Filed: Jan. 22, 2002

(65) Prior Publication Data

US 2002/0102521 A1 Aug. 1, 2002

(30) Foreign Application Priority Data

Jan. 31, 2001 (JP) ........................................ 2001-024129

(51) Int. Cl.$^7$ ................................................. A61C 5/00
(52) U.S. Cl. ...................................................... 433/215
(58) Field of Search ................................. 433/215, 213, 433/223, 24; 705/1, 2, 3

(56) References Cited

U.S. PATENT DOCUMENTS 6,361,318 B1 * 3/2002 Back et al. .................. 433/215

OTHER PUBLICATIONS

U.S. patent application Ser. No. 10/050,956, filed Jan. 22, 2002, pending.

* cited by examiner

*Primary Examiner*—Kevin Shaver
*Assistant Examiner*—Melba Bumgarner
(74) *Attorney, Agent, or Firm*—Oblon, Spivak, McClelland, Maier & Neustadt, P.C.

(57) ABSTRACT

To prepare a dental prosthesis that has a shape exactly the same as in the form at the time of sound state, with superior intra-oral fitness precision, a process for preparing a dental prosthesis utilizing a CAD/CAM system includes subjecting three-dimensional coordinate information of an intra-oral shape measured by impression taking or by photographing within an oral cavity of a patient, to three-dimensional graphic display on a graphic display device and designing a dental prosthesis on the three-dimensional graphic, wherein three-dimensional coordinate information of a previously preserved intra-oral shape of a patient at the time of sound state is subjected to graphic display simultaneously on the graphic display device; the dental prosthesis of an objective tooth is designed so as to have a shape same as the shape at the time of sound state; the obtained design data of the dental prosthesis is transmitted to a milling processor as a processing command; and a block material is subjected to milling processing to prepare a dental prosthesis.

1 Claim, No Drawings

PROCESS FOR PREPARING DENTAL PROSTHESIS

BACKGROUND OF THE INVENTION

1. Field of the Invention

The present invention relates to a process for preparing a dental prosthesis such as an inlay, a crown, and a bridge utilizing a CAD/CAM (computer-aided design and manufacturing) apparatus. In particular, the present invention relates to a process for preparing a dental prosthesis comprising designing of a dental prosthesis using three-dimensional coordinate information taken by measuring an intra-oral shape of a patient himself or herself, which has been previously measured and preserved.

2. Description of the Conventional Art

Hitherto, for the preparation of dental prostheses such as inlays, crowns, and bridges, there has been generally employed a process in which a metal material or a ceramics material is cast by the lost wax casting process. Further, dental prostheses, in which the principal object is placed at aesthetics, such as ceramic inlays and all-ceramic crowns, are prepared by building up a porcelain on a refractory casting material and firing it in a vacuum electric furnace.

Usually, the preparation of dental prostheses by the lost wax casting process is carried out in the following procedures. That is, a prosthesis shape to be restored is prepared using a wax on a plaster model prepared by pouring a gypsum into an impression obtained by impression taking within an oral cavity, followed by curing; the obtained wax pattern is invested in a refractory investment; after curing the investment, the assembly is placed in an electric furnace and heated to burn the wax pattern; a metal or a ceramics material is cast in the obtained casting mold; and after cooling, the cast material is excavated from the investment, cut and polished to prepare a desired dental prosthesis such as an inlay and a crown. Further, in the case of ceramic inlays, all-ceramic crowns and the like, they are prepared in a process in which a duplicated cast is prepared using a refractory casting material; a porcelain is built up on the duplicated cast to form a desired dental prosthesis shape; and after firing in a vacuum firing furnace, the refractory casting material is removed, followed by forming the surface characterization and polishing.

Since the state of an objective tooth (e.g., the state of dental caries, the state of fracture or breakage) and the intra-oral shape vary in patients one by another, a dental prosthesis to be prepared is also different in the patients one by another. Accordingly, the form of the dental prosthesis is designed and prepared based on intuition and experiences of a dental technician while taking into account the relation with antagonists or adjacent teeth or the occlusal relation. Moreover, as described above, the operation for preparing the dental prosthesis is complicated and includes many steps of manual works. Nonetheless, the completed prosthesis is required to have an extremely high dimensional precision in the order of several $\mu$m. Thus, required are not only a skill of the dental technician, but also a long period of time and labors.

Under these circumstances, as a method for supplying dental prostheses having a constant quality within a short period of time stably and in a large quantity, in recent years, a CAD/CAM (computer-aided design and manufacturing) system in which a dental prosthesis such as an inlay, a crown, and a bridge is designed on a screen utilizing a computer and prepared by milling processing is paid attention. Particularly, a design and preparation system of a dental prosthesis using a CAD/CAM system represented by the Cerec system (a system of Siemens AG, Germany) has been paid attention. This CAD/CAM system is a process in which the shape of a tooth subjected to preparation of abutment tooth or cavity preparation and if necessary, the shapes of adjacent teeth or antagonists are read out; a desired dental prosthesis is designed based on the thus read out tooth shape using a computer; and a block-like material such as a resin cured material, a ceramic sintered material, and a metal material is set in a milling processor and subjected to milling processing to prepare the desired dental prosthesis.

In comparison with the casting process as described above, this CAD/CAM system is characterized in that dental prostheses can be prepared with good efficiency; if the design is properly carried out, the completed dental prostheses are high in the precision; and that dental prostheses having superior fitness precision in an oral cavity can be prepared. According to the CAD/CAM system, it is possible to undergo the computation for determining the ultimate shape of the dental prosthesis (converting the shape into information for processing) through automatic computation by a computer. However, since the state of an objective tooth and the intra-oral shape vary in patients one by another, it is necessary to carry out ultimately the design for forming a shape of a dental prosthesis as its basis in a manual manner. In order to design and determine the shape of this dental prosthesis, required are not only a knowledge and technique of a skilled dental technician based on an anatomical shape of the tooth, but also a knowledge and technique for a design operation of highly advanced CAD. It is the present situation that it is difficult to prepare an ideal dental prosthesis having a superior fitness precision because of difficulty of the design operation.

As described above, in the preparation of dental prostheses, which are currently carried out, the shape of a dental prosthesis to be prepared is determined by a dental technician based on overall observation of the shape of adjacent teeth, the dentition shape, the shape of antagonists, the occlusal relation, etc., irrespective of the lost wax casting process and the CAD/CAM system. However, even when a skilled dental technician makes the design, it is impossible to design the shape in a form exactly the same as the form at the time of sound state. Thus, it is the present situation that it is hard to say that ideal dental prostheses are prepared.

SUMMARY OF THE INVENTION

Then, the present invention is aimed to provide a process for a dental prosthesis having an ideal shape for a patient, a good precision and a superior intra-oral fitness, utilizing a preparation process of a dental prosthesis by milling processing by means of a milling processor in a CAD/CAM system, on a basis of a thinking that the shape of a dental prosthesis that is ideal for the patient is designed into a shape exactly the same as the form at the time of sound state.

In order to achieve the above-described aim, we, the present inventors, made extensive and intensive investigations and took note of the matters that the preparation of a dental prosthesis according to the CAD/CAM system is carried out by milling processing based on a design data and that if it is possible to make the design data so as to have a shape exactly the same as the form at the time of sound state, it is possible to prepare a dental prosthesis having a shape exactly the same as the form at the time of sound state. As a result, it has been found that when an intra-oral shape of a patient himself or herself at the time of sound state is previously measured and preserved as a digital signal, and the shape of a dental prosthesis of an objective tooth is designed later during the preparation of a dental restoration using three-dimensional coordinate information taken by measuring the preserved intra-oral shape, it is possible to prepare the shape exactly the same as the form at the time of sound state and that the prepared dental prosthesis is one restored to a state of the shape exactly the same as the form at the time of sound state, leading to accomplishment of the present invention.

Specifically, the process for preparing a dental prosthesis according to the present invention is a process for preparing a dental prosthesis utilizing a CAD/CAM system, which comprises subjecting three-dimensional coordinate information of an intra-oral shape measured on a basis of a plaster model prepared by impression taking within an oral cavity of a patient, or an intra-oral shape measured on a basis of an image taken by photographing within an oral cavity of a patient, to three-dimensional graphic display on a graphic display device and designing a dental prosthesis on the three-dimensional graphic, wherein three-dimensional coordinate information of a previously preserved intra-oral shape of a patient himself or herself at the time of sound state is subjected to graphic display simultaneously on the graphic display device; the dental prosthesis of an objective tooth is designed so as to have a shape the same as the shape at the time of sound state; the obtained design data of the dental prosthesis is transmitted to a milling processor as a processing command; and a block material is subjected to milling processing to prepare a dental prosthesis.

DESCRIPTION OF THE PREFERRED EMBODIMENTS

The process for preparing a dental prosthesis according to the present invention is carried out in the following manner. That is, first of all, an interior of an oral cavity at the time of sound state is subjected to impression taking in a dental office or the like; a sectional and removable type plaster model is prepared; individual teeth of the sectional and removable type plaster model are then fixed on a measuring table using a utility wax, etc.; and three-dimensional coordinate information of the intra-oral shape is obtained using a measuring instrument. Alternatively, an interior of an oral cavity at the time of sound state is photographed using an intra-oral camera or the like in a dental office or the like; and three-dimensional coordinate information of the intra-oral shape is obtained based on the images using a computer, etc. Next, a dentition shape and a dentition shape in an antagonist side are measured to obtain three-dimensional coordinate information. At this time, with respect to the positional relation of dentitions of upper and lower jaws, it is preferred that reference points are previously provided during measuring the plaster models of the upper and lower jaws, and both the reference points of the information as measured for the plaster model of the maxillary dentition and the information as measured for the plaster model of the mandibular dentition are then made to coincide, thereby enabling to subject the positional relation of the dentitions of the upper and lower jaws to graphic display. The thus obtained intra-oral three-dimensional coordinate information in a sound state is stored and preserved in a memory within a computer, or an external preservation medium such as a floppy disc and an MO (magneto-optical) disc, as a digital signal. Since this three-dimensional coordinate information regarding the intra-oral shape is used later during the preparation of a dental prosthesis, the dental office may possess it, or the patient himself or herself may possess it as an external preservation medium and submit it to the dental office or the like during the remedy. In any of these cases, it is preferred that after lapsing a certain period of time, the same operation is carried out again, thereby renewing the intra-oral three-dimensional coordinate information.

And, in the case where a dental caries or breakage or fracture actually occurs so that it becomes necessary to prepare an intra-oral prosthesis, first of all, an intra-oral dental shape or dentition shape of a patient is subjected to impression taking using a dental impression material in a dental office or the like, to prepare a plaster model. For example, in the case where a No. 6 crown in the left side of a mandibula of a patient is prepared using a resin material, dentition shapes of a formed abutment tooth (No. 6 in the left side of the mandibula) and its adjacent teeth (Nos. 5 and 7 in the left side of the mandibula) and a dentition shape of antagonists (a dentition in a counterpart relation with an objective side, such as Nos. 5 to 7 etc. in the left side of the maxillary) are subjected to impression taking using a dental silicone impression material or the like, and respective sectional and removable type plaster model are prepared using a dental plaster. Here, as the abutment tooth, included are not only the case of one prepared by cutting and forming a crown or dental root portion of a natural tooth, but also the case where a lower structure of a dental prosthesis fixed in an intra-oral side of an implant fixture embedded within a mandible of a deficient tooth portion is fixedly adhered.

Next, the abutment tooth portion of the sectional and removable plaster model is fixed on a measuring table using a dental utility wax, etc., and three-dimensional coordinate information of the abutment tooth is measured using a measuring instrument. Then, three-dimensional coordinate information regarding the dentition shape in the abutment tooth side and the dentition shape in the antagonist side is measured. At this time, with respect to the positional relation of dentitions of upper and lower jaws, it is preferred that reference points are previously provided during measuring the plaster models of the upper and lower jaws, and both the reference points of the information as measured for the plaster model of the maxillary dentition and the information as measured for the plaster model of the mandibular dentition are then made to coincide, thereby enabling to subject the positional relation of the dentitions of the upper and lower jaws to graphic display.

As the measuring instrument, used is preferably a laser type measuring instrument as a non-contact type measuring instrument. In the case where the laser type measuring instrument is used, when the plaster model is colored black, the scatter of the laser beams can be reduced, and hence, such is preferred. After completion of the measurement of the shape of the plaster model, the obtained three-dimensional coordinate information is stored in a memory within a computer, or an external preservation medium such as a floppy disc and an MO (magneto-optical) disc, as a digital signal.

On the other hand, as the method for obtaining three-dimensional coordinate information of an intra-oral shape as measured based on images taken by photographing an interior of an oral cavity of a patient, first of all, the interior of the oral cavity of the patient is photographed using an intra-oral camera as generally employed in the dental office or the like, in various directions to the objective tooth, to take a plurality of images (preferably, from 5 to 6 pieces of images). Next, the measurement is carried out by conversion processing into a three-dimensional data using a computer on a basis of these images, to obtain three-dimensional coordinate information regarding the intra-oral shape.

Next, on a basis of the three-dimensional coordinate information regarding the intra-oral shape, a dental prosthesis, which will have a shape of an ideal dental prosthesis, is designed based on the three-dimensional graphic of the intra-oral shape displayed on a graphic display device such as a CRT (cathode ray tube) screen of a computer. Specifically, first of all, the three-dimensional graphic of the shape of the abutment tooth is displayed on the graphic display device, and if desired, the shape of the adjacent teeth or antagonists of the abutment tooth is subjected to three-dimensional graphic display. And, the previously preserved three-dimensional coordinate information regarding the intra-oral shape of a patient himself or herself at the time of sound state is simultaneously subjected to graphic display on the graphic display device, and a dental prosthesis of an objective tooth is designed into a crown shape exactly the same as the shape at the time of sound state. Thereafter, the occlusal relation is simulated on the graphic display device, and the relation with the antagonists, such as a contact point, is confirmed, thereby determining the crown shape. Further, in the case where the dental prosthesis is a bridge, it is necessary to design a deficient tooth portion, too. In this case, a contact point is provided at an arbitrary position of a visible outline of the crown positioned in the both sides of the deficient tooth portion as designed by the foregoing method, and the deficient tooth portion (pontic portion) is designed based on the tooth shape at the time of sound state. Then, on the graphic display device, the relation with the antagonists is adjusted, and the placement and removal direction is confirmed, thereby determining the bridge shape.

Next, carried out are a design operation for making a margin of the dental prosthesis coincide with a margin line of the abutment tooth and a design operation for securing a cement space in the dental prosthesis. Specifically, the design is carried out such that a visible outline of the margin of the dental prosthesis is deformed based on the shape of the abutment tooth with respect to the dental prosthesis displayed in three-dimensional graphic manner on the graphic display device, thereby making the margin of the dental prosthesis coincide with the margin line of the abutment tooth. Thereafter, in order to secure a cement layer, the design is carried out in such a manner that an offset is made corresponding to a certain site and thickness. Incidentally, with respect to the constant site and thickness for securing the cement layer, preferred is a site positioned above the margin portion by about 0.2 to 2 mm and a thickness of about 20 to 150 $\mu$m generally. When the shape of the dental prosthesis has been determined, a quality, a size, etc. of a block material to be processed are set up on the graphic display device, and a rest, which will be a support portion during the processing, is added on the display device. The rest is corresponding to a sprue line of the casting and displayed in a cylindrical shape in a three-dimensional graphic manner on the graphic display device. And, the movement, the rotation and the change of diameter are carried out using a device such as a mouse, and the rest is set up at an optimum position from the viewpoint of the shape while avoiding the occlusal surface and the margin portion. Thereafter, the size of the material as set up by means of automatic processing by a computer is compared with the size of the dental prosthesis to be prepared. In the case where the dental prosthesis as designed is larger than the material to be used, the position of the rest to be set up is changed, or the material that is intended to use is changed to one having a larger size. Thus, after the conditions for designing the dental prosthesis have been determined, ultimate automatic computation by the computer (so-called computation of CAD) is carried out. The design data as the result of the computation is stored in a memory within a computer, or an external preservation medium such as a floppy disc and an MO disc, as a digital signal.

The thus obtained design data is transmitted as a processing command to an NC (numerical control) milling processor. Simultaneously, the block material to be used is chosen and installed in an automatic milling, and then subjected to milling processing based on the design data using milling tools such as a diamond bar and a carbide bar, to prepare the dental prosthesis. Since the obtained dental prosthesis is designed so as to have a shape exactly the same as in a state of a sound tooth, based on the intra-oral shape of a patient at the time of sound state, it is superior in the fitness precision and good in the occlusion state and is an ideal dental prosthesis restoring the sound state.

As described above in detail, the process for preparing a dental prosthesis according to the present invention is concerned with the preparation of a dental prosthesis utilizing a CAD/CAM system, which comprises designing a shape of a dental prosthesis of an objective tooth based on three-dimensional coordinate information of a previously preserved intra-oral shape of a patient himself or herself at the time of sound state, thereby enabling to prepare a dental prosthesis exactly the same as the format the time of sound state. When the obtained dental prosthesis is set within an oral cavity, the interior of the oral cavity in the sound state is reproduced. The dental prosthesis as prepared by the process of the present invention is superior in the fitness precision and good in the occlusion state. Thus, the process for a dental prosthesis having the various advantages as described according to the present invention is greatly valuable in contribution to the dental field.

While the invention has been described in detail and with reference to specific embodiments thereof, it will be apparent to one skilled in the art that various changes and modifications can be made therein without departing from the spirit and scope thereof.

What is claimed is:

1. A process for preparing a dental prosthesis utilizing a CAD/CAM system, which comprises subjecting three-dimensional coordinate information of an intra-oral shape measured on a basis of a plaster model prepared by impression taking within an oral cavity of a patient, or an intra-oral shape measured on a basis of an image taken by photographing within an oral cavity of a patient, to three-dimensional graphic display on a graphic display device and designing a dental prosthesis on the three-dimensional graphic display, wherein three-dimensional coordinate information of a previously preserved intra-oral shape of a patient himself or herself at the time of sound state is subjected to graphic display simultaneously on the graphic display device; the dental prosthesis of an objective tooth is designed so as to have a shape the same as the shape at the time of sound state; design data of the dental prosthesis is transmitted to a milling processor as a processing command; and a block material is subjected to milling processing to prepare a dental prosthesis.

* * * * *